United States Patent [19]

Trouet

[11] 4,277,466
[45] Jul. 7, 1981

[54] COMPLEXES OF DNA AND ESTERS DERIVED FROM DAUNORUBICINE, THEIR PREPARATION AND USE

[75] Inventor: André Trouet, Winksele, Belgium

[73] Assignee: Institut International de Pathologie Cellulaire et Moléculaire, Brussels, Belgium

[21] Appl. No.: 67,511

[22] Filed: Aug. 17, 1979

[30] Foreign Application Priority Data

Aug. 29, 1978 [BE] Belgium ............................... 870026

[51] Int. Cl.³ ...................... A61K 31/71; C07H 15/24
[52] U.S. Cl. ................................ 424/180; 536/17 A; 536/22; 536/28; 536/29
[58] Field of Search ...................... 424/180; 536/17 A

[56] References Cited

U.S. PATENT DOCUMENTS

| | | | |
|---|---|---|---|
| 3,803,124 | 4/1974 | Arcamone et al. | 536/17 A |
| 4,031,211 | 6/1977 | Patelli et al. | 536/17 A |
| 4,127,714 | 11/1978 | Umezawa et al. | 536/17 A |

FOREIGN PATENT DOCUMENTS 1440626  6/1976  United Kingdom ...................... 536/17

OTHER PUBLICATIONS

Di Marco et al. "Chem. Abst", vol. 75, 1971 p. 71329y.

Primary Examiner—Johnnie R. Brown

[57] ABSTRACT

A complex of deoxyribonucleic acids (DNA) with an ester derived from daunorubicine of the formula

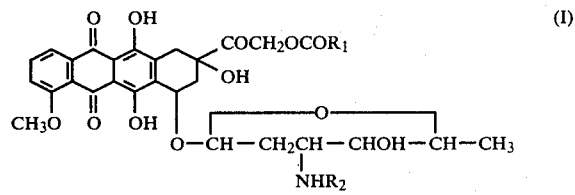

in which $R_1$ represents a radical of the formula

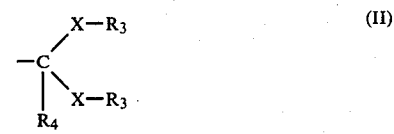

in which each X represents oxygen or sulfur and each $R_3$ represents alkyl, phenyl or both $R_3$ form together with one another an alkylene group, $R_4$ is hydrogen, alkyl or phenyl and $R_2$ is hydrogen or trifluoracetyl.

Said complexes are usable for treating cancerous tumors.

5 Claims, No Drawings

COMPLEXES OF DNA AND ESTERS DERIVED FROM DAUNORUBICINE, THEIR PREPARATION AND USE

The present invention relates to complexes of esters derived from daunorubicine, their preparation and pharmaceutical compositions containing such complexes.

More particularly, the present invention has for its object complexes of deoxyribonucleic acids (DNA) with ester derivatives of daunorubicine of the general formula:

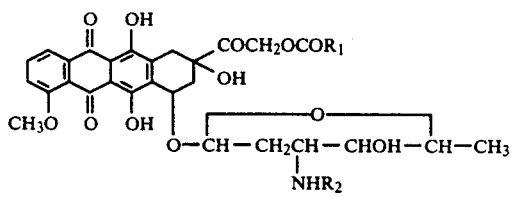

wherein $R_1$ represents a group of the formule

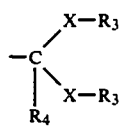

wherein the symbols X each represent an oxygen or sulfur atom and are identical to one another and the symbols $R_3$ represent alkyl groups containing 1 to 4 carbon atoms, phenyl groups which may carry in para-position a methyl, methoxy or methylthio substituent group or form together with one another an alkylene group containing 2 to 4 carbon atoms, the symbol $R_4$ represents a hydrogen atom or an alkyl group containing 1 to 4 carbon atoms or a phenyl group and the symbol $R_2$ represents a hydrogen atom or a trifluoroacetyl group. Alternatively, the symbols X are different from one another, in which case the symbols $R_3$ form together with one another an alkylene group containing 2 to 4 carbon atoms.

The complexes according to the present invention can be prepared by adding under sterile conditions to DNA dissolved in sterile aqueous sodium chloride solution without pyrogenic matter, an aqueous solution of ester of the general formula I prepared extemporaneously.

Practically there is used DNA type VII sigma in the sodium form originating from herring sperm. Said DNA is dissolved into a 0.15 M solution of sodium chloride at a concentration close to $2.10^{-3}$ g/cm$^3$. In order to facilitate dissolution of DNA, it is particularly advantageous to heat the mixture for 5 minutes at a temperature close to 100° C.

The solution obtained is filtered by means of a 0.8 micron Millipore filter and then sterilized by treatment in an autoclave at a temperature of about 120° C. for about 15 minutes.

After cooling of the solution obtained, one adds aseptically a solution of a salt, generally the hydrochloride, of an ester of the formula I in sterile distilled water or in a 0.15 M aqueous solution of sodium chloride at a concentration of about 0.03 mole/cm$^3$.

The solution of DNA and ester are mixed in amounts such that the molar ratio between the DNA mononucleotide and the ester is between 10/1 and 40/1, preferably of about 20/1.

The complexes according to the invention show outstanding antitumoral properties together with a toxicity less than that of the corresponding non-complexed esters. They have proved active against leukemia L 1210 grafted intravenously or subcutaneously in DBA$_2$ mice in doses between 9 and 35 mg/kg a day when administered for two days intravenously.

The toxicity of the complexes according to the invention has been determined in NMRI mice by intravenous route after two intravenous injections at 24 hours interval of time.

The LD$_{50}$ (30 days) values are substantially higher than those of non-complexed esters.

There may be specially mentioned a complex of ADN with 14-diethoxyacetoxy daunorubicine, an ester of formula I in which $R_2$ represents hydrogen and $R_1$ represents

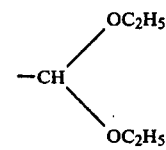

Said complex has a toxicity corresponding to the LD$_{50}$ (50% lethal dose) of 25.9 mg/kg i.v. in NMRI mice. When treating with said complex in a dose of 15 mg/kg applying two treatments at 24 hours interval of time, DBA$_2$ mice inoculated subcutaneously with 10$^5$ cells of L 1210, the number of mice remaining in life after 30 days is quadrupled with respect to the number of mice treated with equitoxic doses of 14-diethoxyacetoxy daunorubicine alone.

The following non-limiting example shows how the invention can be put into practice.

EXAMPLE 20 mg of 14-diethoxyacetoxy daunorubicine hydrochloride are dissolved into 1 cm$^3$ of sterile distilled water. 234 mg of sodium ADN of herring sperm (type VII Sigma Chemical Co., St. Louis, Mo., U.S.A.) are on the other hand dissolved into 100 cm$^3$ of a sterile solution without pyrogenic matter containing 9 g of sodium chloride per liter. The solution of ADN is heated for 5 minutes at 100° C. and then filtered when still being hot through a 0.8 micron Millipore filter. The filtrate is put again into an autoclave and maintained at 120° C. for 15 minutes and then cooled slowly to about 20° C. The solution of 14-diethoxyacetoxy daunorubine is added aseptically to 99 cm$^3$ of sterile DNA solution. One obtains in that way 100 cm$^3$ of a solution containing 25 mg of 14-diethoxyacetoxy daunorubicine complexed with 231.6 mg of DNA.

The pharmaceutical compositions can be used for the treatment of Leukemia L 1210. These compositions comprise complexes of DNA with esters of the general formula I in the form of aqueous sterile solutions ready for use or in lyophilized form to be dissolved at the moment of use in sterile distilled water.

The preferred administration form is the parenteral, more particularly intravenous route.

What I claim is:

1. An antitumoral complex of DNA and 14-diethoxyacetoxy daunorubicin.

2. A complex according to claim 1 wherein the molar ratio of DNA, expressed as mononucleotide, to 14-diethoxyacetoxy daunorubicin is from about 10:1 to 40:1.

3. A complex according to claim 2 wherein the said molar ratio is about 20:1.

4. A complex according to claim 1 wherein the DNA is of type VII Sigma.

5. Pharmaceutical composition which contains a pharmaceutically effective amount of a complex as defined in claim 1 in lyophilized (freeze-dried) form or in solution in a pharmaceutically acceptable diluent or solute.

* * * * *